US007204159B2

(12) United States Patent
Hasegawa

(10) Patent No.: US 7,204,159 B2
(45) Date of Patent: Apr. 17, 2007

(54) FASTENING MEMBER REMOVING FORCE MEASURING DEVICE AND HOLDING DEVICE

(75) Inventor: Kenji Hasegawa, Fujisawa (JP)

(73) Assignee: YKK Corporation, Tokyo (JP)

( * ) Notice: Subject to any disclaimer, the term of this patent is extended or adjusted under 35 U.S.C. 154(b) by 0 days.

(21) Appl. No.: 11/115,456

(22) Filed: Apr. 27, 2005

(65) Prior Publication Data

US 2005/0241125 A1 Nov. 3, 2005

(30) Foreign Application Priority Data

Apr. 30, 2004 (JP) .............................. 2004-135909

(51) Int. Cl.
  *G01L 5/00* (2006.01)
  *G01N 3/08* (2006.01)
(52) U.S. Cl. .................... 73/862.01; 73/826; 73/788; 73/760; 73/856; 73/831; 73/862
(58) Field of Classification Search ................. 73/761, 73/856
See application file for complete search history.

(56) References Cited

U.S. PATENT DOCUMENTS

| | | | | | |
|---|---|---|---|---|---|
| 2,220,962 | A | * | 11/1940 | Kingman | 38/66 |
| 2,588,420 | A | * | 3/1952 | Shaw | 19/252 |
| 4,596,349 | A | * | 6/1986 | Herten | 227/18 |
| 5,819,381 | A | * | 10/1998 | Lake | 24/564 |
| 6,012,215 | A | * | 1/2000 | DeMoura | 29/505 |
| 6,662,666 | B2 | * | 12/2003 | Hasegawa | 73/831 |

FOREIGN PATENT DOCUMENTS

JP 09-037811 2/1997

OTHER PUBLICATIONS

"SORBOTHANEâ Standard Products & Price Guide" Jan. 3, 2003 <http://web.archive.org/web/20030409230421/http://sorbothane.com/PDF/StandardProduct.pdf>.*

* cited by examiner

Primary Examiner—Edward Lefkowitz
Assistant Examiner—Punam Patel
(74) Attorney, Agent, or Firm—Everest Intellectual Property Law Group; Michael S. Leonard

(57) ABSTRACT

The fastening member removing force measuring device according to the present invention includes a holding unit (300) for holding and pressing a fabric (953) around a snap member (921), a restricting unit for restricting the snap member (921), and a tensile force measuring unit for pulling the restricting unit away from the fabric (953) and measuring a tensile force. The holding unit (300) includes a die (420) for mounting thereon the fabric 953, and a fabric presser unit (500) for holding the fabric (953) placed on the die (420) together with the die (420). The die (420) includes a frame holding section (430) having an open face opposite to the fabric presser unit (500) and also having an accommodating section (434) inside thereof, a viscoelastic section (440) provided inside the accommodating section (434), and an elastic section (450) laminated on the viscoelastic section (440) in the accommodating section (434) on the side of the fabric presser unit (500) and formed with an elastic member harder than the viscoelastic member (440).

10 Claims, 15 Drawing Sheets

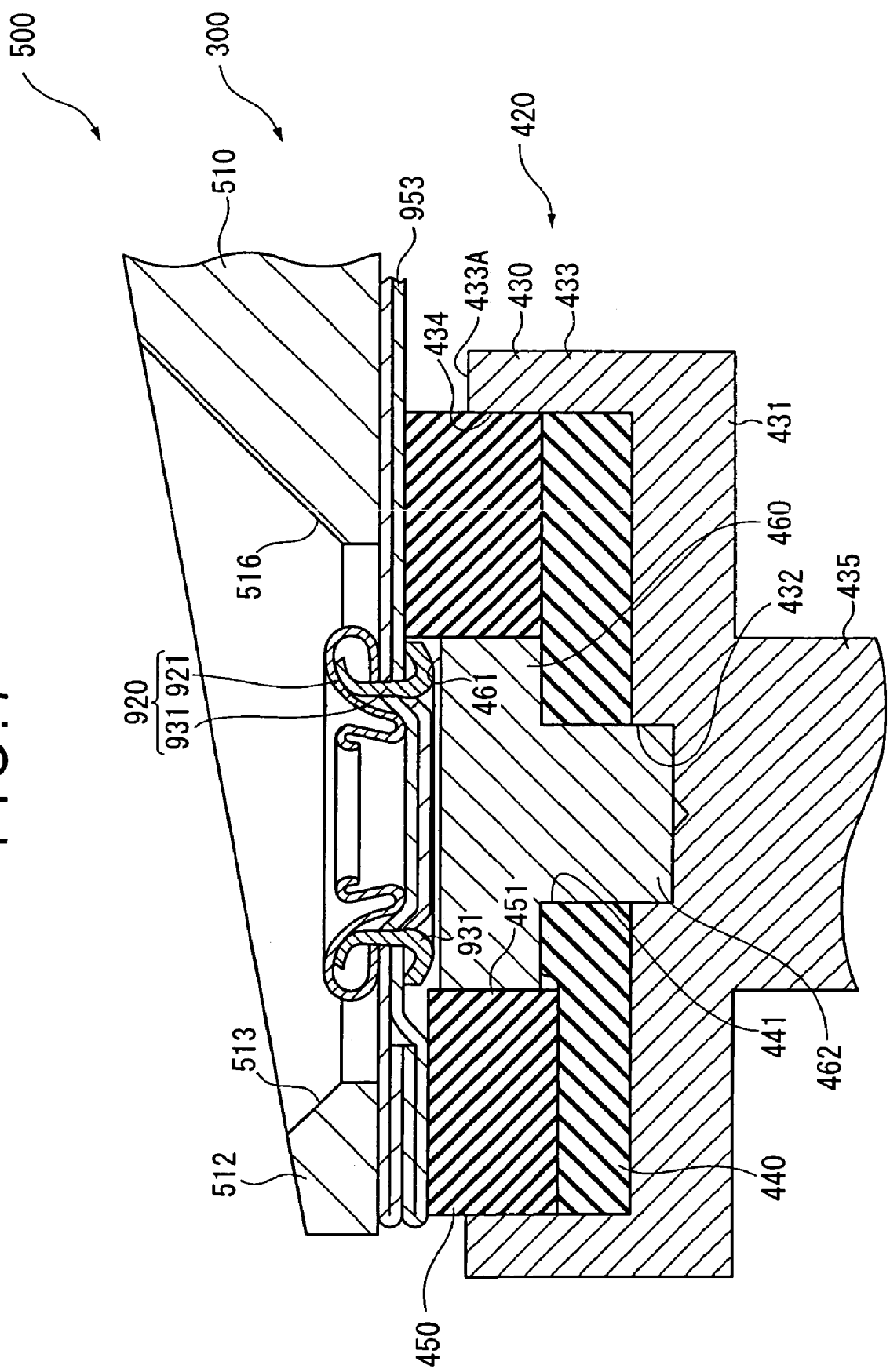

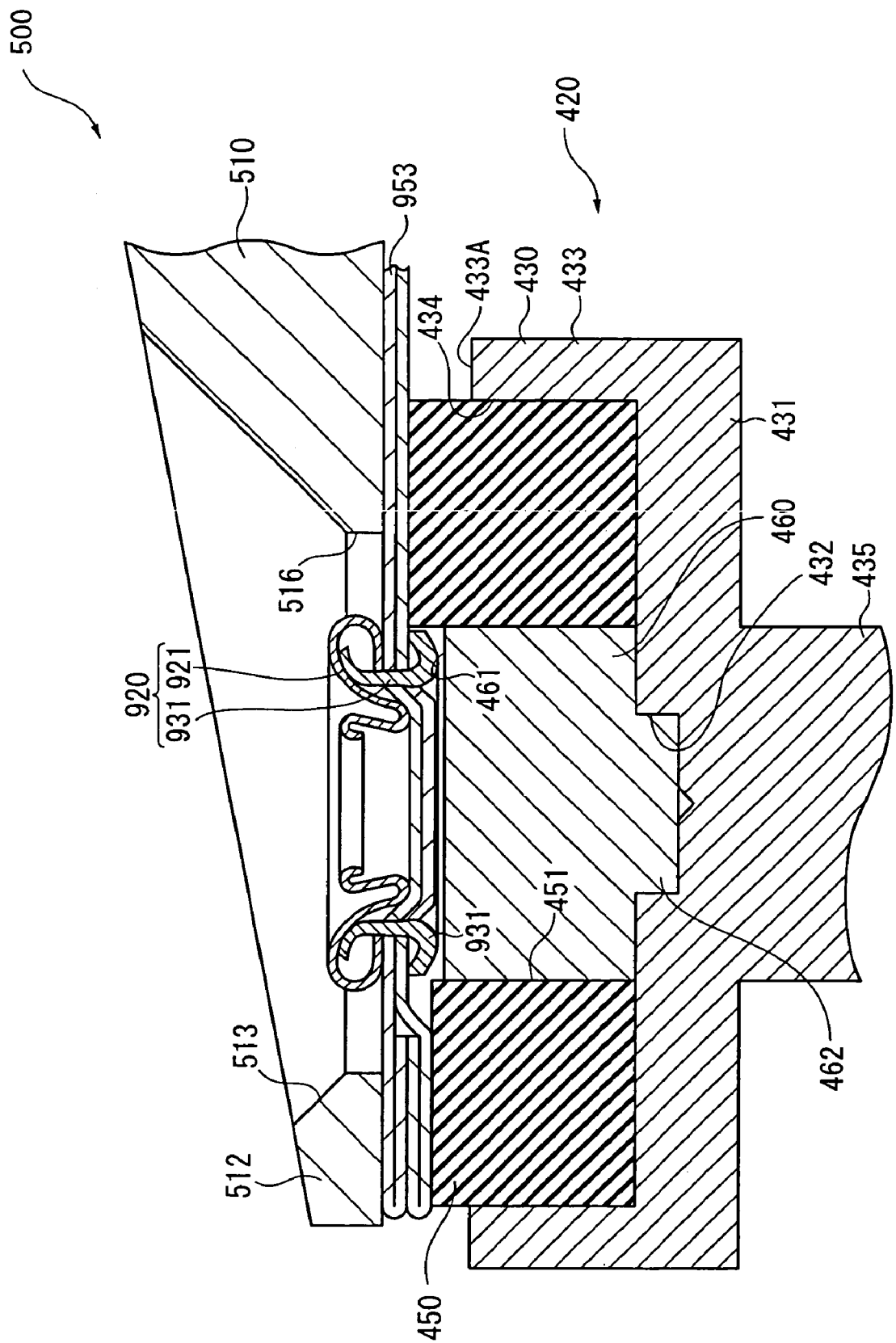

FASTENING MEMBER REMOVING FORCE MEASURING DEVICE AND HOLDING DEVICE

BACKGROUND OF THE INVENTION

1. Field of the Invention

The present invention relates to a fastening member removing force measuring device, and a holding device. More specifically, this invention relates to a removing force measuring device for measuring a force required for removing, for instance, a snap member attached to a garment.

2. Description of Related Art

To fasten a fastening section 910 of a garment 900, a snap fastener 920, for instance, is used as shown in FIG. 10. The snap fastener 920 includes, as shown in FIG. 11, a female snap member 930 generally called as a socket member, a male snap member 940 generally called as a stud (these two components are generically called as a snap member 921), and prong members 931, 941 each attaching the snap member 921 to the fabric.

The male snap member 940 and the female snap member 930 can elastically and disconnectably be engaged with each other, and are respectively and opposingly attached to a first fabric 951 and a second fabric 952 in the fastening section 910 of the garment 900. For instance, as shown in FIG. 11, the female snap member 930 and male snap member 940 are respectively attached to opposing surfaces of the fabric 952, 951 with the prong members 931, 941 from the sides reverse to the opposing surfaces.

If the snap member 921 attached to a fabric 953 of the garment 900 is easily removed from the fabric 953, there occurs the risk, for instance, that an infant swallows the snap member 921 (930, 940) or the prong members 931, 941, so that a force required to remove the snap member 921 must be set at a level not less than a prespecified value. To satisfy this requirement, for instance in a sewing plant, inspections are conducted for a force required for removing the snap member 921 so that the force required for removing the snap member 921 are kept not less than the prespecified value.

Sewing companies comply with the European standard "BS EN 71-1: Safety of toys. Mechanical and physical properties" in various countries, and the force required for removing the snap member 921 is required to be "90 N for 10 seconds" or more.

In the conventional technology, there has been the configuration shown in FIG. 12 and FIG. 13 as a measuring device for measuring a force required for removing the snap member 921 (refer to, for instance, Reference: Japanese Patent No. 3328473).

FIG. 12 is a side view showing a snap member removing force measuring device, and FIG. 13 is a partially enlarged view of the snap member removing force measuring device when viewed from the front side.

A removing force measuring device 800 includes a stage 400 for mounting thereon the snap member 921 attached to a fabric 953, a fabric presser unit 500 for pressing the fabric 953 around the snap member 921 mounted on the stage 400, a restricting unit 600 for restricting a side face of the snap member 921, and a tensile force measuring section 700 for pulling the restricting unit 600 restricting the snap member 921 in a direction away from the fabric presser unit 500 and also measuring this tensile force.

The stage 400 has a die 420 supported by a supporting block 413 via a spring section 415 having a plurality of plate springs.

The fabric presser unit 500 includes a fabric presser arm 510 with a substantially intermediate section thereof swingably supported at an upper end of a support member 520 and having a ring section 512 for pressing the fabric 953 around the snap member 921 at a tip thereof.

The restricting unit 600 has jaws 610, 610 each having a tip engagement section 611 capable of being engaged with a side face of the snap member 921 provided at a tip thereof with the tip engagement sections 611 provided circularly and surrounding the snap member 921; a jaw supporting member 620 for swingably supporting an intermediate section of the jaws 610 so that the tip engagement sections 611 of the jaws 610 move closer to or away from each other, a spring 630 for biasing each jaw 610 in a direction in which the tip engagement sections 611 of the jaws 610 move away from each other; and a cum section 640 contacting a base end 612 of each jaw 610 for rotating each jaw in a direction in which the tip engagement sections 611 of each jaws 610 get closer to each other.

The tensile force measuring section 700, though not described in detail herein, pulls up the restricting unit 600 restricting the snap member 921 by pulling up a bolt 641 extending upward from the jaw supporting member 620 of the restricting unit 600 and measures the tensile force in the state.

With the configuration as described above, when a force required for removing the snap member 921 is to be measured, first, the snap member 921 attached to the fabric 953 is placed on the die 420. In the state where the snap member 921 is placed inside the ring section 512 of the fabric presser arm 510, the fabric 953 is held by the ring section 512 of the fabric presser arm 510 and the die 420. The cum section 640 with the bolt 641 screwed therein is rotated to be lowered so that the tip engagement sections 611 of the jaws 610 get closer to each other and also so that the base end 612 of the jaw 610 is pushed and opened by the cum section 640, and in this state a side face of the snap member 921 is restricted by the jaws 610 with the tip engagement section 611. In this state, when the snap member 921 restricted by the jaws 610 is slowly pulled up, the snap member 921 is pulled from the fabric 953 and lifted upward, since the fabric 953 is held by the fabric presser arm 510 and the die 420. The force required for pulling up the snap member 921 is measured by the tensile force measuring section 700, and if the snap member 921 is kept attached to the fabric 953 even when the force required for pulling up the snap member 921 is over a prespecified value, the prespecified removing force is ensured. Further, if the snap member 921 is lifted up until being removed off from the fabric 953, a removing force for the snap member 921 can be measured.

An edge of the garment (indicated by a reference numeral 960 in FIG. 10) is sewn in the state where the fabric 953 is rolled in to prevent the fabric 953 from being frayed. Therefore, the rolled-in portion has a larger thickness as compared to that of the other portion as shown in FIG. 14. In this state, if the snap fastener 920 is provided on a thin portion of the fabric 953 near the edge section 960, and both the thick portion of the fabric 953 and the thin portion of the fabric 953 are held with the fabric presser arm 510 and the die 420, the thick portion of the fabric 953 is held strongly but the thin portion of the fabric 953 is not held, resulting in that the fabric 953 can not be held properly, as shown in FIG. 15. Namely a gap d is generated between the fabric presser arm 510 and the thin portion of the fabric 953.

Unless the fabric 953 is held tightly, when the snap member 921 is pulled up, also the fabric 953 is pulled, so that the snap member 921 is hardly removed from the fabric 953, and therefore the removing force can not correctly be measured, which is disadvantageous.

Generally, since the snap member 921 is attached to a position as close as possible to an edge of the garment 900 to minimize opening of the fastening section 910, it is often required to measure a removing force for the snap member 921 attached to a position close to a step between portions having different thicknesses of the fabric 953 when the removing force for the snap member 921 is to be measured.

SUMMARY OF THE INVENTION

An object of the present invention is to provide a fastening member removing force measuring device capable of accurately measuring a removing force for a fastening member and a holding device for appropriately holding and pressing a fabric having different thicknesses at different portions.

The fastening member removing force measuring device according to an aspect of the present invention is used for measuring a force required for removing a fastening member attached to a fabric, and the removing force measuring device includes a holding unit for holding and pressing the fabric around the fastening member; a restricting unit for restricting the fastening member; and a tensile force measuring unit for pulling at least either one of the restricting unit and the holding unit in a direction in which the restricting unit restricting the fastening member and the holding unit move away from each other and measuring a tensile force, in which the restricting unit includes a die for mounting thereon the fabric with the fastening member attached thereto; and a fabric presser unit for pressing the fabric mounted on the die to the die to hold the fabric together with the die, and the die includes a frame holding section with a face facing the fabric presser unit opened and having an accommodating section inside thereof; a viscoelastic section provided in the accommodating section, and an elastic section laminated on the viscoelastic section in the accommodating section and provided on the side of the fabric presser unit, the elastic section formed with an elastic member harder than the viscoelastic section.

With the configuration as described above, when a force required to remove a fastening member is to be measured, first, in the state where a fabric is held by the holding unit, the fastening member is restricted by the restricting unit. Then in the state where the fabric is held by the holding unit, the restricting unit is pulled by the tensile force measuring unit in a direction in which the restricting unit moves away from the fabric for measuring the removing force. A removing force for the fastening member is then measured as described above.

To accurately measure the removing force for the fastening member, it is necessary to tightly hold the fabric with the holding unit so that the fabric does not move even when the fastening member is pulled. However, sometimes it is required to hold a fabric having different thicknesses in the right and left portions thereof with the holding unit. In such case, even if a thick portion of the fabric can be tightly held with the die and the fabric presser unit, a clearance may be generated between the fabric presser unit and a thin portion of the fabric. However, since the viscoelastic portion deforms according to a difference in thickness, both the thick portion and thin portion can tightly be held by the die and the fabric presser unit.

Further, a face contacting the fabric requires to be hard to some extent to hold and fix the fabric tightly, while the face requires to be deformable to some extent in accordance with a thickness of the fabric to hold a fabric having different thicknesses in different portions.

With the present invention, the face contacting the fabric is a hard elastic section, so that the fabric can tightly be held. Further the viscoelastic section has the elastic and viscous properties, and because of its behavior like that of a viscous fluid, the viscoelastic section can deform according to a difference in thickness of the fabric. Therefore, even if the fabric has different thicknesses in different portions, both a thick portion and a thin portion of the fabric can appropriately be held and fixed. As a result, the fabric is tightly fixed, so that a removing force for a fastening member can accurately be measured.

The fastening member includes, but not limited to, a snap member or a button member attached to a fabric, a prong member or a rivet for fastening a snap member or a button member to a fabric.

The viscoelastic section may a viscoelastic member, or a sealed sol or fluid having the viscoelastic property.

The hard elastic section is harder than the viscoelastic section, and may include, for instance, hard rubber, plastic, thermosetting elastomer, thermoplastic elastomer, or a plate spring formed with a thin metallic plate.

Hardness of the viscoelastic section is, for instance, shore 30 to shore 70 as expressed by the shore 00 scale. Further a loss factor of the viscoelastic section (tan $\delta$) is, for instance, in the range substantially from 0.5 to 1.5 at the room temperature (20° C.).

The holding unit preferably holds any portion of the fabric around the fastening member with the substantially same holding force.

With the configuration as described above, when the fastening member is pulled up by the tensile force measuring unit while the fastening member is restricted by the restricting unit, a portion of the fabric held with a weak holding force is prevented from being raised together with the fastening member. Namely, the fastening member is evenly removed from the fabric when the fabric is pulled up, so that a removing force for the fastening member can accurately be measured.

In the present invention, it is preferable that an elastic holding member made of an elastic member is provided on a face of the fabric presser unit contacting the fabric.

With the configuration as described above, as the face contacting the fabric is an elastic member, a frictional force generated when the fabric is held with the elastic holding member and the die (elastic section) becomes larger, so that the fabric can be fixed more tightly.

In the present invention, it is preferable that a protruding section and a concave section engaging with each other are provided on faces of the fabric presser unit and the elastic section facing each other respectively.

With the configuration as described above, when the fabric is held with the fabric presser unit and the die, the fabric is bitten by the protruding section and the concave section, so that the fabric is fixed more tightly.

A holding device according to another aspect of the present invention is used for holding a fabric, and includes a die for mounting thereon the fabric with a fastening member attached thereto; and a fabric presser unit for pressing the fabric mounted on the die to the die from a side opposite to the die and holding the fabric with the die, in which the die includes a frame holding section with a face facing the fabric presser unit opened and having an accommodating section inside thereof; a viscoelastic section provided in the accommodating section; and an elastic section laminated on the viscoelastic section in the accommodating section and provided on the side of the fabric presser unit and, the elastic section formed with an elastic member harder than the viscoelastic section.

With the configuration as described above, the same effects as those provided by the invention described above are provided. Namely, the viscoelastic section deforms according to a thickness of a fabric, so that both a thick portion and a thin portion of the fabric can tightly be held by the die and the fabric presser unit.

Further, since the face contacting a fabric is a hard elastic section, so that the fabric is held tightly. In addition, the face deforms according to a difference in thickness of the fabric because of the behavior of the viscoelastic section like that of a viscous fluid. Therefore, even if a fabric has different thicknesses in different portions, both a thick portion and a thin portion of the fabric can appropriately be held by the holding unit, so that the fabric is fixed tightly.

BRIEF DESCRIPTION OF THE DRAWINGS

FIG. 7 is a view showing a variant of the present invention in which an elastic ring member is not provided therein;

FIG. 8 is a view showing a variant of the present invention in which one layer of a hard elastic section is provided;

DETAILED DESCRIPTION OF PREFERRED EMBODIMENT(S)

Figure 1:
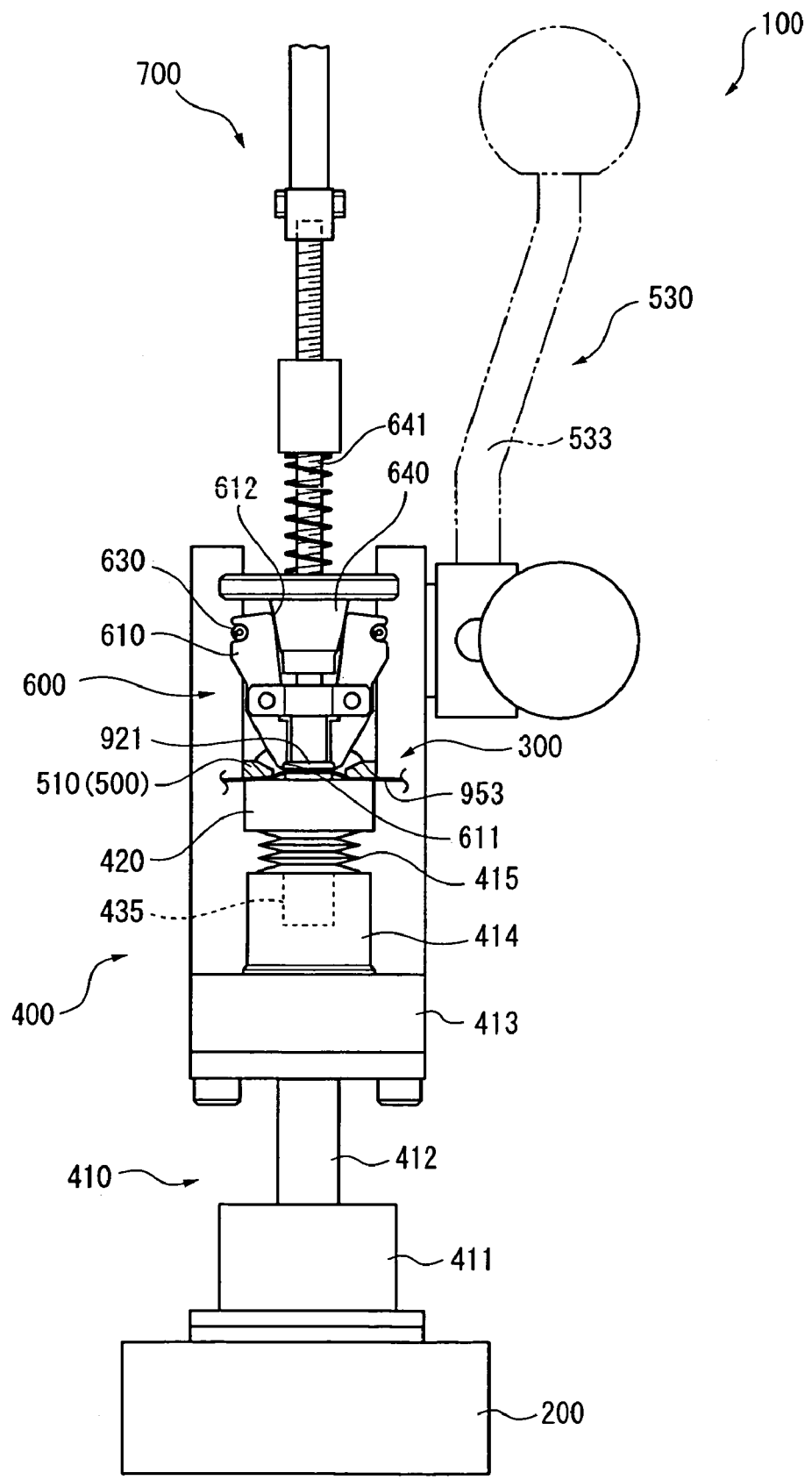
FIG. 1 is a front view showing a removing force measuring device according to a first embodiment of the present invention.

Embodiments of the present invention will be described below with reference to reference numerals assigned to the components respectively in the figures.

(First Embodiment)

A fastening member removing force measuring device according to a first embodiment of the present invention will be described below.

Figure 2:
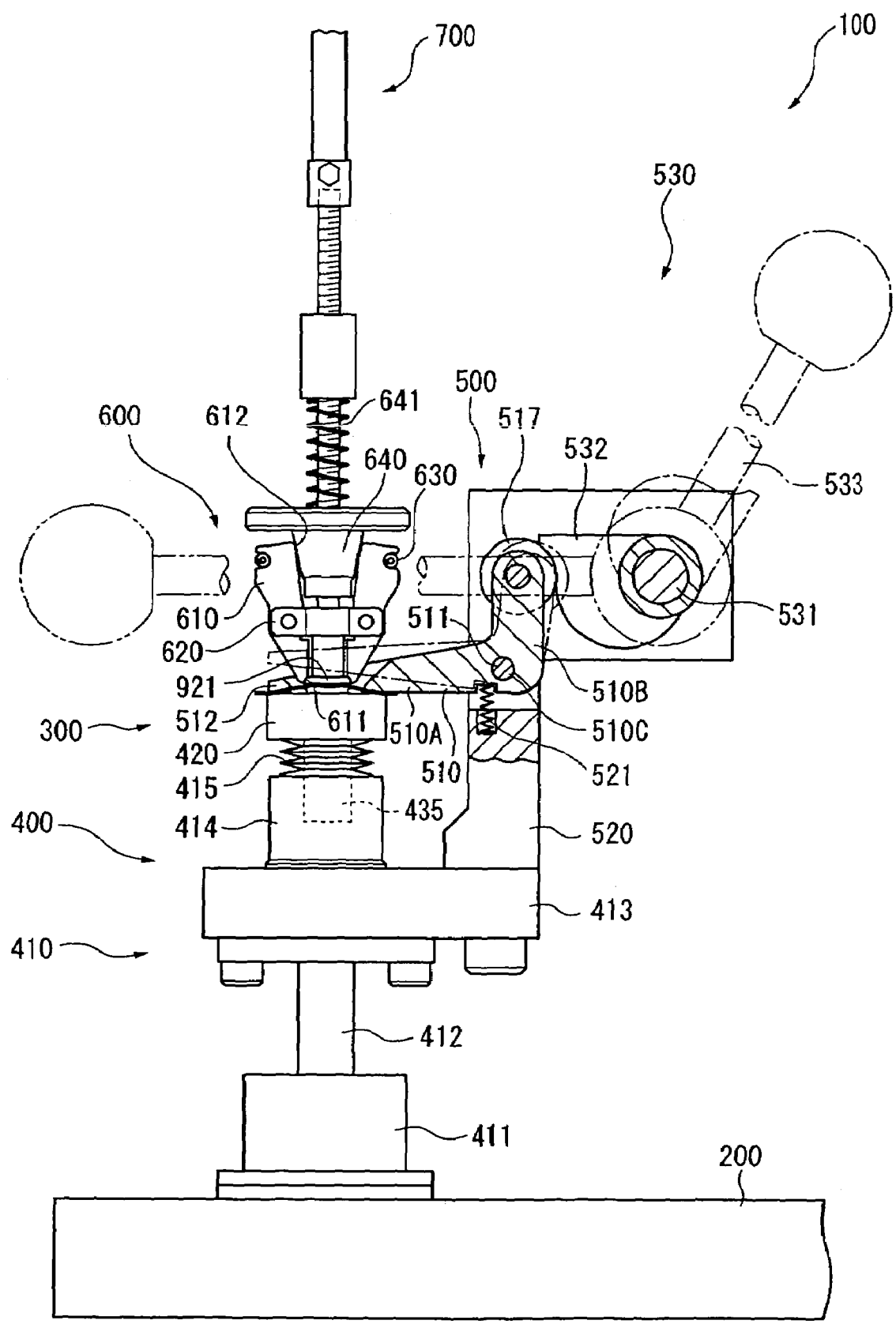
FIG. 2 is a side view showing the removing force measuring device according to the first embodiment.

FIG. 1 is a front view showing a removing force measuring device, while FIG. 2 is a side view showing the removing force measuring device.

A removing force measuring device 100 includes a base 200, a holding unit (holding device) 300 provided in the upright posture on the base 200 for holding the fabric 953 with the snap member (fastening member) 921 attached thereto, a restricting unit 600 for holding and restricting the snap member 921 from a side thereof, and a tensile force measuring section (tensile force measuring unit) 700 for pulling up the restricting unit 600 restricting the snap member 921 and measuring a tensile force in the pulling operation.

Figure 3:
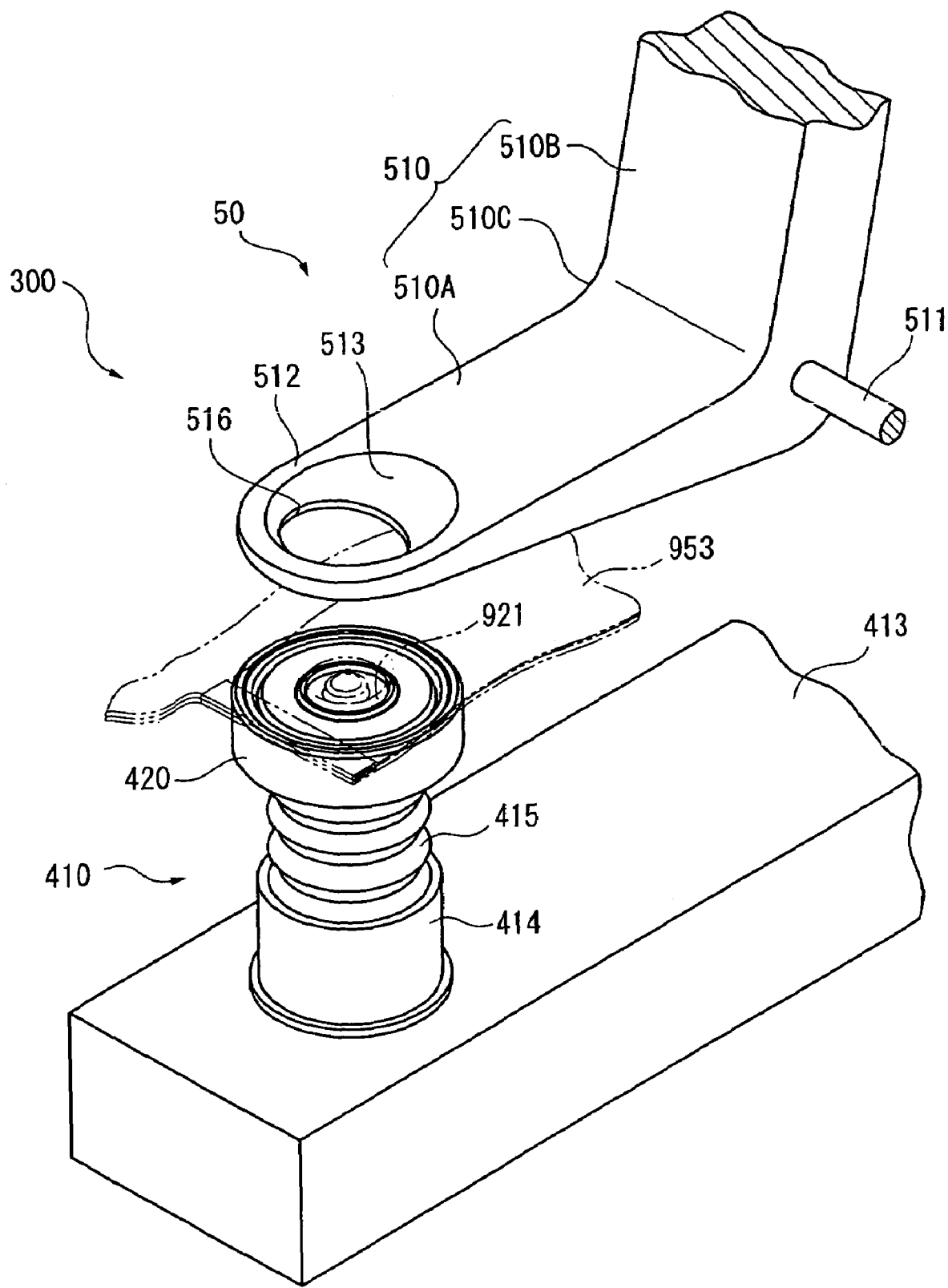
FIG. 3 is a perspective view showing a holding unit in the first embodiment.
Figure 4:
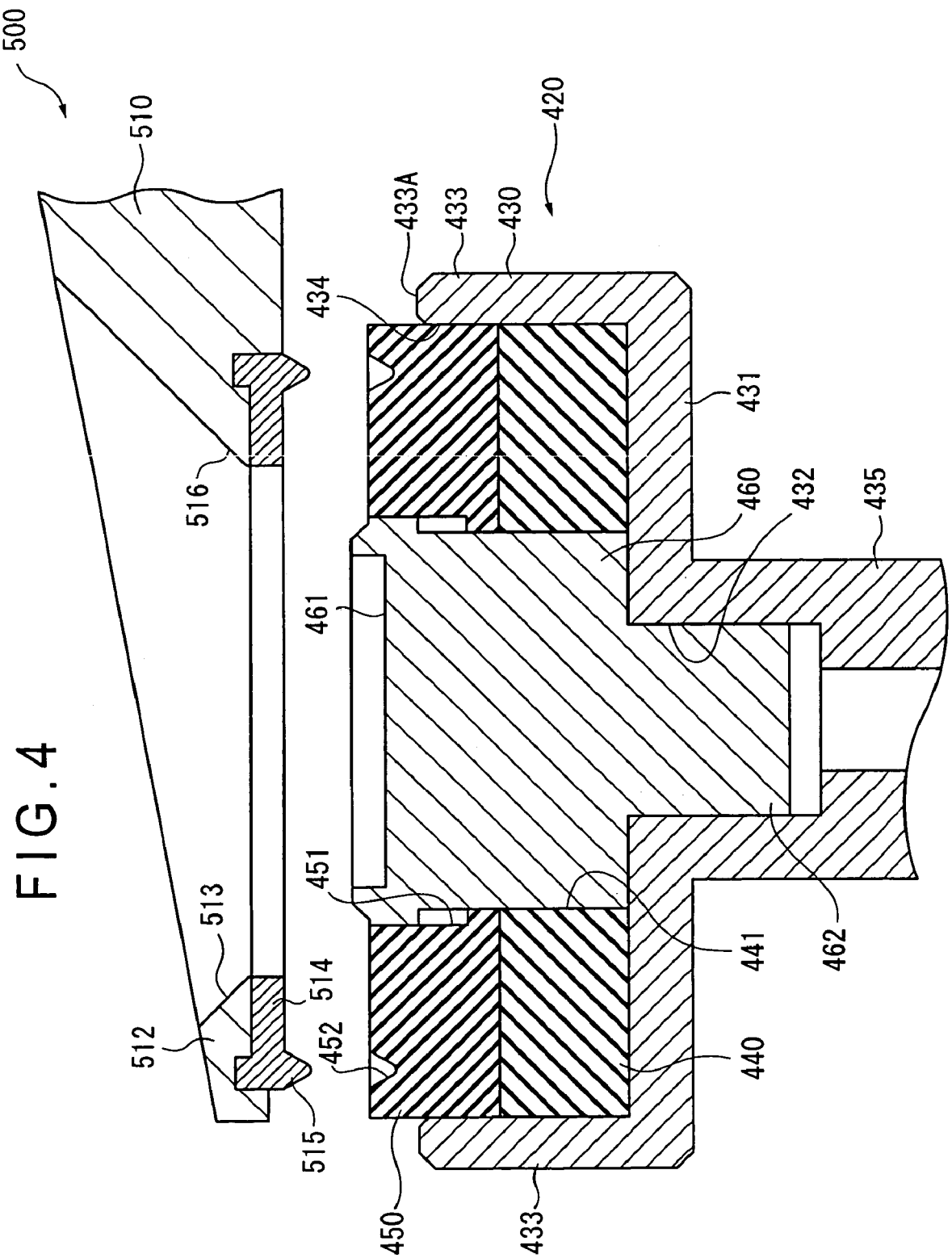
FIG. 4 is a cross section showing the holding unit according to the first embodiment.
Figure 5:
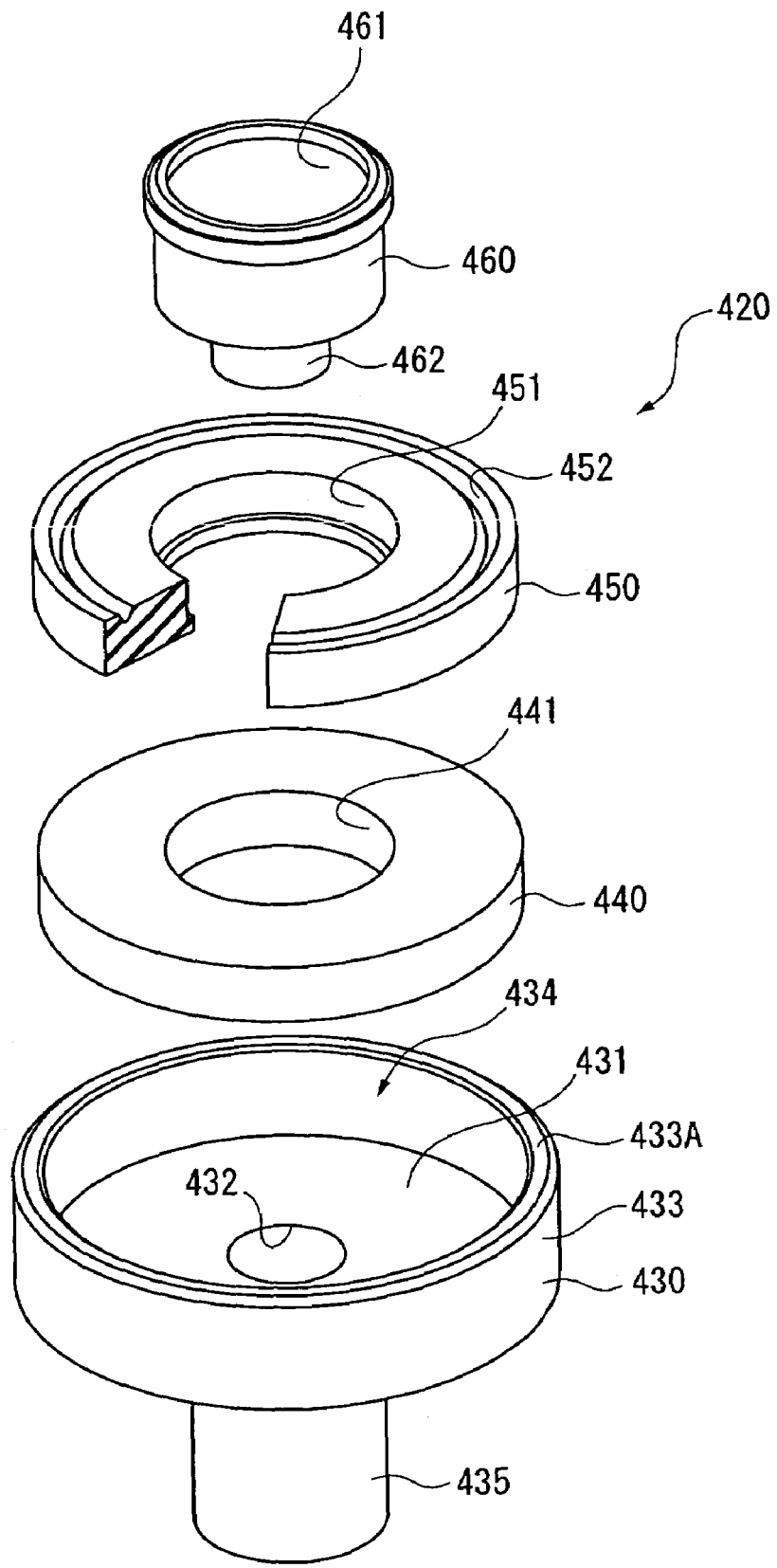
FIG. 5 is an exploded perspective view showing a die in the first embodiment.

FIG. 3 is a perspective view showing the holding unit 300, FIG. 4 is a cross section showing the holding unit 300, and FIG. 5 is an exploded perspective view showing the die 420.

The holding unit 300 includes a stage 400 functioning as a mounting for mounting the fabric 953, and a fabric presser unit 500 for pressing the fabric 953 mounted on the stage 400 from a side opposite to the stage 400 to hold the fabric 953 together with the stage 400.

The stage 400 includes a supporting section 410 provided in the upright posture on the base 200, and a die 420 functioning as a mounting supported by the supporting section 410 for mounting thereon the fabric 953.

The supporting section 410 includes a supporting bench 411 fixed on an upper surface of the base 200, a supporting block 413 supported by the supporting bench 411 via a supporting bolt 412, a pedestal 414 fixed on the supporting block 413, and a spring section 415 having plate springs alternately laminated on the pedestal 414 each in a reverse direction.

The die 420 includes a substantially cylindrical bottomed frame holding section 430, for instance, with an upper face thereof opened and having an accommodating section 434 inside thereof, a viscoelastic section 440 and hard elastic section (elastic section) 450 respectively having center holes 441, 451 and successively laminated inside the accommodating section 434 of the frame holding section 430, and a mounting base 460 engaged with the center holes 441, 451 of the viscoelastic section 440 and the hard elastic section 450.

The frame holding section 430 includes a substantially circular bottom plate section 431 having a center hole 432 at a substantially central position, a peripheral wall section 433 monolithically provided in the upright posture along a periphery of the bottom plate section 431 and surrounding the accommodating section 434 with a face opposite to the bottom plate section 431 opened, and a base shaft section 435 having a hole communicated to the center hole 432 of the bottom plate section 431 and extending in a direction opposite to that in which the peripheral wall section 433 stands.

Figure 6:
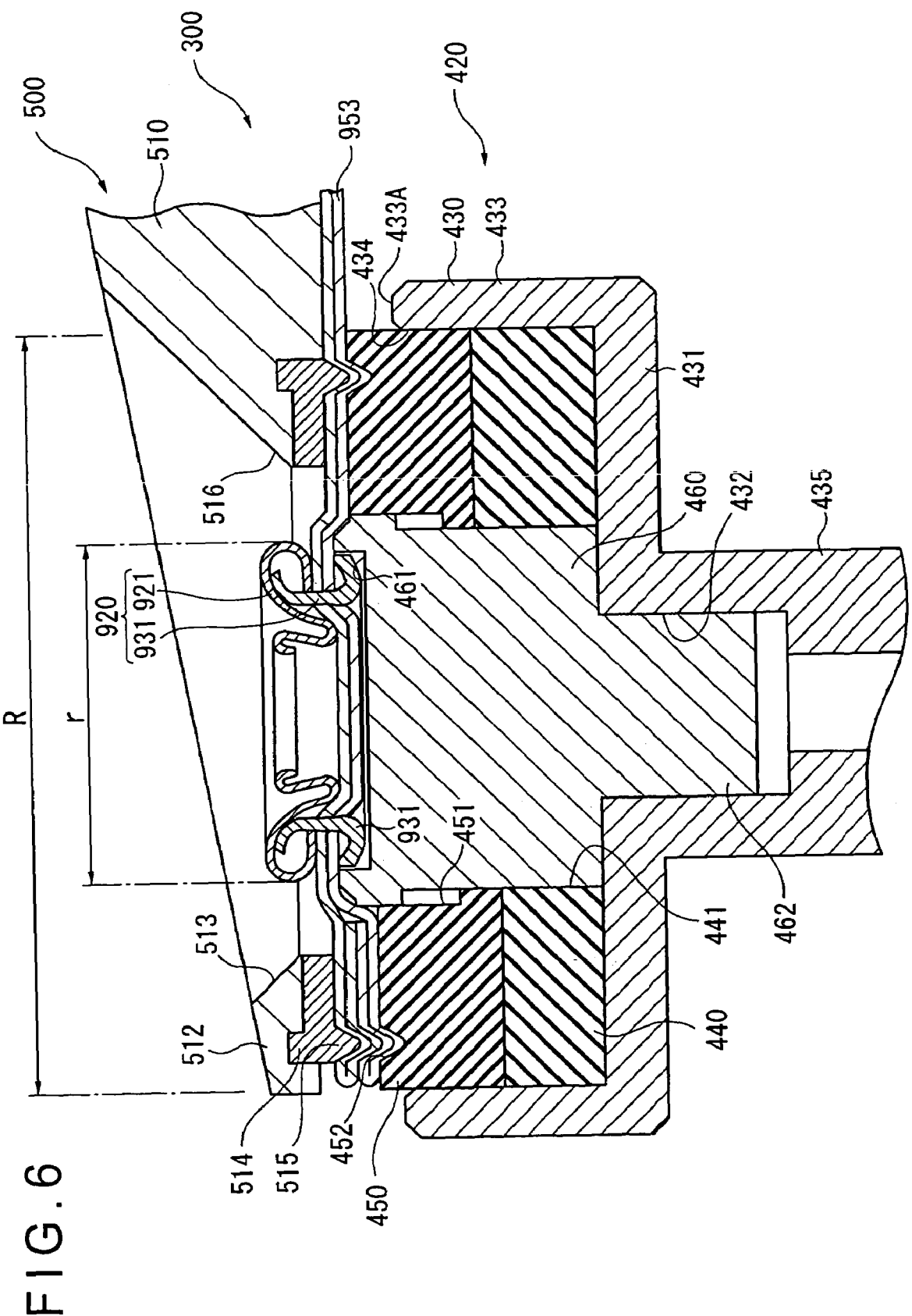
FIG. 6 is a cross section showing the state where a fabric having different thicknesses in both sides of a snap member is held by the holding unit according to the first embodiment.

The frame holding section 430 is substantially cylindrical, and an inner diameter R of the accommodating section 434 is around two times larger than a diameter r of the snap member 921 (refer to FIG. 6). The frame holding section 430 is supported by the pedestal 414 via the spring section 415, and the base shaft section 435 penetrates the spring section 415 to be engaged with the pedestal 414 (refer to FIG. 1 and FIG. 2).

The viscoelastic section 440 has a donut-like form having the center hole 441 at the central portion, and is inserted into the accommodating section 434 of the frame holding section 430, and the viscoelastic section 440 is held between the hard elastic section 450 inserted into the accommodating section 434 from an upper side of the viscoelastic section 440 and the bottom plate section 431.

The viscoelastic section 440 has the properties of viscosity and elasticity, which is capable of relaxing a stress when a stress is loaded thereto, because distortion caused by the stress gradually approaches (creeps to) the equilibrium. The viscoelastic section 440 is formed, for instance, with viscous polyurethane (refer to Japanese Patent Publication No. S62-26330, Japanese Patent Publication No. H6-92478) or viscoelastic elastomer, and with SORBO (registered trademark). Hardness of the viscoelastic section 440 is, for instance, shore 30 to shore 70 as expressed by the shore 00 scale, and further a loss factor of the viscoelastic section 440 (tan δ) is, for instance, in the range substantially from 0.5 to 1.5 at the room temperature (20° C.).

The hard elastic section 450 has a donut-like form having the center hole 451 at the central position, and is inserted into the accommodating section 434 of the frame holding section 430 from an upper side of the viscoelastic section 440.

The hard elastic section 450 is formed with an elastic member harder as compared to the viscoelastic section 440, which shows less elastic deformation as compared to the viscoelastic section 440, when a force is loaded thereto. The hard elastic section 450 is formed, for instance, with thermoplastic elastomer.

When the hard elastic section 450 is inserted into the accommodating section 434 of the frame holding section 430, an upper surface of the hard elastic section 450 protrudes slightly upward from an opening periphery 433A of the peripheral wall section 433. Further a circular groove (concave section) 452 concentric to the center hole 451 is grooved at a position relatively close to the outer peripheral on the upper surface of the hard elastic section 450.

The viscoelastic section 440 and hard elastic section 450 are accommodated within the accommodating section 434 of the frame holding section 430 substantially without any clearance.

The mounting base 460 has a substantially cylindrical form, and when inserted into the center holes 451, 441 of the hard elastic section 450 and viscoelastic section 440, an upper surface of the mounting base 460 is on the substantially same plane as the upper surface of the hard elastic section 450.

The outer periphery of the upper surface of the mounting base 460 is slightly raised to form a concave section functioning as the mounting concave section 461 for mounting thereon the snap member 921 and the prong member 931 (941).

A monolithically-formed and shaft-formed insertion/engagement shaft section 462 extends from a bottom surface of the mounting base 460, and when this insertion/engagement shaft section 462 is engaged with and fixed to the base shaft section 435 of the frame holding section 430, the mounting base 460 is fixed in the accommodating section 434 of the frame holding section 430.

The fabric presser unit 500 is swingably supported and includes a fabric presser arm 510 for pressing the fabric 953 with a ring section 512 at a tip thereof, a support member 520 provided in the upright posture on the supporting block 413 and swingably supporting the fabric presser arm 510 with a tip thereof, and an operating unit 530 for operating the swinging movement of the fabric presser arm 510.

The fabric presser arm 510 is a member having a substantially L-shape, and in this fabric presser arm 510, an active shaft portion 510A provided in the substantially horizontal posture and an operating shaft portion 510B provided in the substantially vertical posture are monolithically provided to form a substantially L-shape at a bending position 510C.

The bending position 510C of the fabric presser arm 510 is supported at an upper end of the support member 520 by a supporting shaft 511, and the active shaft portion 510A can be raised from the substantially horizontal posture as the base state. When the fabric presser arm 510 oscillates, a tip of the active shaft portion 510A moves away from an upper surface of the die 420.

By forming a hole 516, a circular ring section 512 is provided at a tip of the active shaft portion 510A. The hole 516 in the ring section 512 has a form having a taper 513 with a diameter becoming larger upward.

An elastic ring member (elastic holding member) 514 having a circular form and surrounding the hole 516 is provided on a bottom surface of the ring section 512, and the elastic ring member 514 has a protruding stripe (protruding section) 515 formed in a ring form and surrounding the hole 561. The elastic ring member 514 is formed, for instance, with thermoplastic elastomer.

The protruding stripe 515 is formed at a position corresponding to the groove 452 provided on the upper surface of the hard elastic section 450, and when the ring section 512 contacts the upper surface of the die 420, the protruding stripe 515 is engaged with the groove 452.

A diameter of the hole 516 of the ring section 512 is slightly larger than a diameter of the mounting base 460, and in the state where the snap member 921 is placed on a mounting concave section 461 of the mounting base 460, when the fabric presser arm 510 oscillates and a tip of the active shaft portion 510A moves toward the die 420, the snap member 921 is positioned inside the hole 516 of the ring section 512, and the fabric 953 is held by (the lower surface of) the ring section 512 and (the upper surface of) the hard elastic section 450.

The support member 520 is provided in the upright posture on the supporting block 413 substantially in parallel to the supporting section 410. The fabric presser arm 510 is swingably supported by the supporting shaft 511 at the upper end of the support member 520, and also a spring 521 for biasing the active shaft portion 510A upward (in the direction in which the active shaft portion 510A moves away from the die 420) is provided between the support member 520 and the active shaft portion 510A.

The operating unit 530 includes an operation lever 533 rotatably provided, and a cum 532 rotating in association with rotation of the operation lever 533 for pressing an end of the operating shaft portion 510B via a bearing 517.

The cum 532 presses via the bearing 517 the end of the operating shaft portion 510B when the operation lever 533 is rotated downward. Then the fabric presser arm 510 is swung around the supporting shaft 511 as a supporting point according to the principle of leverage with a tip of the active shaft portion 510A moving toward the die 420, and thus the ring section 512 strongly presses the upper surface of the die 420 downward.

Configuration of a restricting unit 600 is substantially the same as that described in relation to the background technology, and includes three jaws 610, a jaw supporting member 620, a spring 630, and a cum section 640, the restricting unit 600 provided in the hung state just above the die 420.

A tensile force measuring section 700 is provided in the upright posture on the base 200, although not shown specifically, and when the bolt 641 extending from the jaw supporting member 620 of the restricting unit 600 is raised upward, the restricting unit 600 restricting the snap member 921 is pulled up, and a tensile force in this state is measured.

Operations of the removing force measuring device 100 having the configuration as described above will be described below.

The following description assumes a case in which the snap fastener 920 (snap member 921, prong members 931, 941) is provided at an edge section 960 of the fastening section 910 of a garment 900, and thicknesses of the fabric 953 in the two sides of the snap fastener 920 are different.

First, the snap fastener 920 (snap member 921, prong members 931, 941) attached to the fabric 953 is placed on the mounting concave section 461 in the mounting base 460. Then the operation lever 533 is rotated to lower the fabric presser arm 510. In this state, the operating shaft portion 510B is pressed by the cum 532 with the fabric presser arm 510 swung. Then the active shaft portion 510A is lowered toward the die 420, and the fabric 953 is pressed to the upper surface of the die 420 by a tip section of the active shaft portion 510A. In this state, the fabric 953 is held by the elastic ring member 514 and the upper surface of the die 420.

FIG. 6 is a cross section showing the state in which the fabric 953 having different thicknesses in two sides of the snap member 921 is held by the holding unit 300 (die 420, fabric presser unit 500).

In FIG. 6, a left side of the fabric 953 is thick because four sheets of the fabric are laminated, and a right side of the fabric 953 is thin.

When the fabric 953 having different thicknesses in the two sides is pressed by the elastic ring member 514 to the upper surface of the die 420 (the upper surface of the hard elastic section 450), the hard elastic section 450 and viscoelastic section 440 deform according to the thicknesses in the two sides, so that the two sides of the fabric 953 are appropriately held by the elastic ring member 514 and the upper surface of the die 420.

When the fabric 953 having a certain thickness is pressed by the elastic ring member 514 to the upper surface of the die 420, the hard elastic section 450 elastically deforms (mainly by bending) almost without changing the thickness so that only the portion just below the thick portion of the fabric 953 is pushed downward, and the viscoelastic section 440 below the hard elastic section 450 is pressed by the hard elastic section 450 and deforms.

In this state, due to the viscous (fluid) property of the viscoelastic section 440, the distortion caused by stress gradually gets closer (creeps) to the equilibrium value, so that the stress gradually decreases as time passes (stress relaxation), and a repelling force (restoring force based on elasticity) acting from the viscoelastic section 440 to the hard elastic section 450 is equalized everywhere after a certain period of time (for instance, after several seconds). Because of this mechanism, both a thick portion and a thin portion of the fabric 953 are held by the elastic ring member 514 and the upper surface of the hard elastic section 450 with a substantially even force.

Further the protruding stripe 515 of the elastic ring member 514 and the groove 452 of the hard elastic section 450 are engaged with each other, and the fabric 953 is held by and fixed between the two components.

Then a side face of the snap member 921 is restricted by the restricting unit 600. Namely, the base end 612 of the jaw 610 is pushed and opened by the cum section 640, and the side face of the snap member 921 is restricted by the tip engagement section 611 of the jaw 610 and with the jaw 610.

In this state, the restricting unit 600 restricting the snap member 921 is pulled up by the tensile force measuring section 700. As the fabric 953 is held by and fixed between the elastic ring member 514 and the die 420, only the snap member 921 is raised. The tensile force in this state is measured by the tensile force measuring section 700. When the snap member 921 is removed from the prong member (931, 941) and is also removed from the fabric 953, a removing force for the snap member 921 is measured.

With the configuration according to the first embodiment, there are provided the following effects and advantages.

(1) Even the fabric 953 having different thicknesses in different portions can tightly be held by the holding unit 300, a removing force for the snap member 921 can accurately be measured.

(2) In the conventional technology, when the fabric 953 having different thicknesses in different portions is held with the holding unit 300, even if a thick portion of the fabric 953 can be held with the die 420 and the fabric presser unit 500, a clearance may be generated between a thin portion of the fabric 953 and the fabric presser arm 510. However, with the present invention, since the viscoelastic section 440 deforms according to a thickness of a portion, also the thin portion of the fabric can be held tightly with the die 420 and the fabric presser arm 510.

(3) As a face contacting the fabric 953 is the hard elastic section 450, the fabric 953 can tightly be held, and in addition, the viscoelastic section 440 can deform according to a thickness of the fabric 953. Therefore, even in a case of the fabric 953 having different thicknesses in different portions, both the thick portion and thin portion of the fabric 953 can appropriately be held and fixed by the holding unit 300 (fabric presser unit 500 and die 420).

(4) Both the thick portion and thin portion of the fabric 953 can be held by the elastic ring member 514 and the upper surface of the hard elastic section 450 with the substantially even force. In the conventional technology, if a removing force for the snap member 921 is large, when the snap member 921 is to be raised, the fabric 953 may be displaced from the holding unit 300 (from between the fabric presser arm 510 and the die 420), and may be raised from the hole 516 of the fabric presser arm 510 together with the snap member 921. However, in the present invention, a force for holding the fabric 953 is even around the snap member 921, so that the fabric 953 is almost evenly raised together with the snap member 921 around the snap member 921. As a result, the prong member (931, 941) inserted into the snap member 921 is removed evenly, so that a removing force for the snap member 921 can accurately be measured.

(5) Since the elastic ring member 514 is provided on the bottom surface of the ring section 512, a frictional force generated when the fabric 953 is held by the elastic ring member 514 and the hard elastic section 450 becomes larger, so that the fabric 953 can tightly be fixed.

(6) Since the protruding stripe 515 is provided on the elastic ring member 514 and further the groove 452 is provided on the hard elastic section 450, when the fabric 953 is held by the elastic ring member 514 and the hard elastic section 450, the fabric 953 is bitten by the protruding stripe 515 and the groove 452, so that the fabric 953 can be fixed more tightly.

The present invention is not limited to the embodiment described above, and modifications and improvements in a range in which the objects of the present invention can be achieved are included in the present invention.

In the embodiment described above, a case in which the holding unit 300 holds the fabric around the snap member 921 (fastening member) along the entire periphery is described, but the fabric 953 may be held not only around the entire periphery of the snap member 921, but also at a plurality of points around the snap member 921. For instance, the fabric 953 may be held at two points opposite to each other around the snap member 921 with the snap member 921 therebetween, or at three points with an angular space of 60 degrees therebetween around the snap member 921, or four points with an angular space of 90 degrees therebetween.

In the embodiment described above, the elastic ring member 514 is provided on the bottom surface of the ring section 512, but, for instance, the elastic ring member 514 may not be provided as shown in FIG. 7. The elastic ring member 514 is formed, for instance, with the same material as that of the hard elastic section 450.

In the embodiment described above, the protruding stripe 515 and the groove 452 are provided on faces of the fabric presser arm 510 and the hard elastic section 450 opposite to each other respectively, but the protruding stripe 515 and the groove 452 as described above may not be provided.

In the embodiment, the viscoelastic section 440 and the hard elastic section 450 are accommodated substantially without any clearance inside the accommodating section 434 of the frame holding section 430, but there may be a clearance to some extent. When there is a clearance, the deformation of the viscoelastic section 440 and hard elastic section 450 can easily be performed.

In the embodiment described above, the viscoelastic section 440 and hard elastic section 450 have a monolithic and donut-like form, but may be divided to a plurality of portions.

In the embodiment described above, the viscoelastic section 440 and hard elastic section 450 are laminated in the accommodating section 434 of the frame holding section 430, but, for instance, only one layer of the hard elastic section 450 may be provided therein as shown in FIG. 8.

Figure 9A:
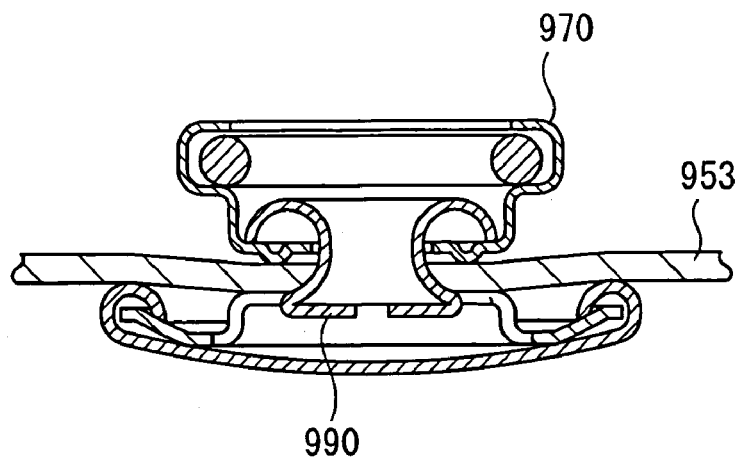
FIG. 9A to FIG. 9C are views each showing a variant of a fastening member according to the present invention.
Figure 9B:
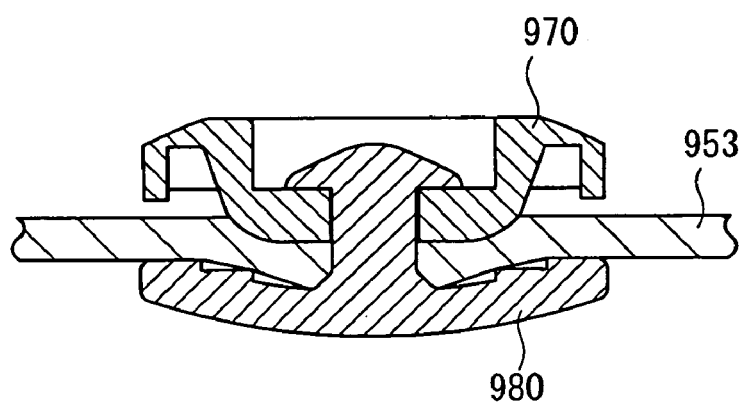
Figure 9C:
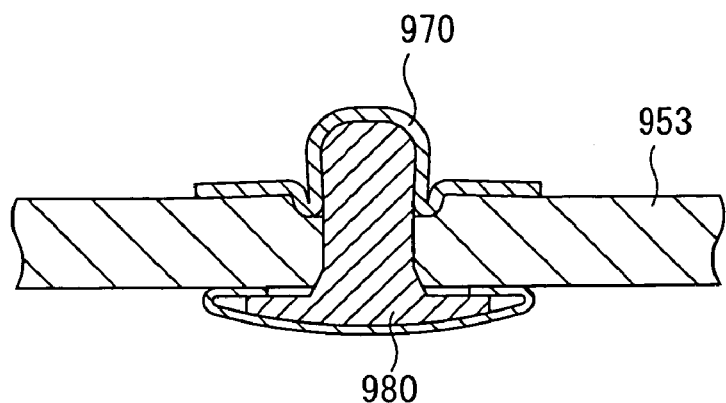
Figure 10:
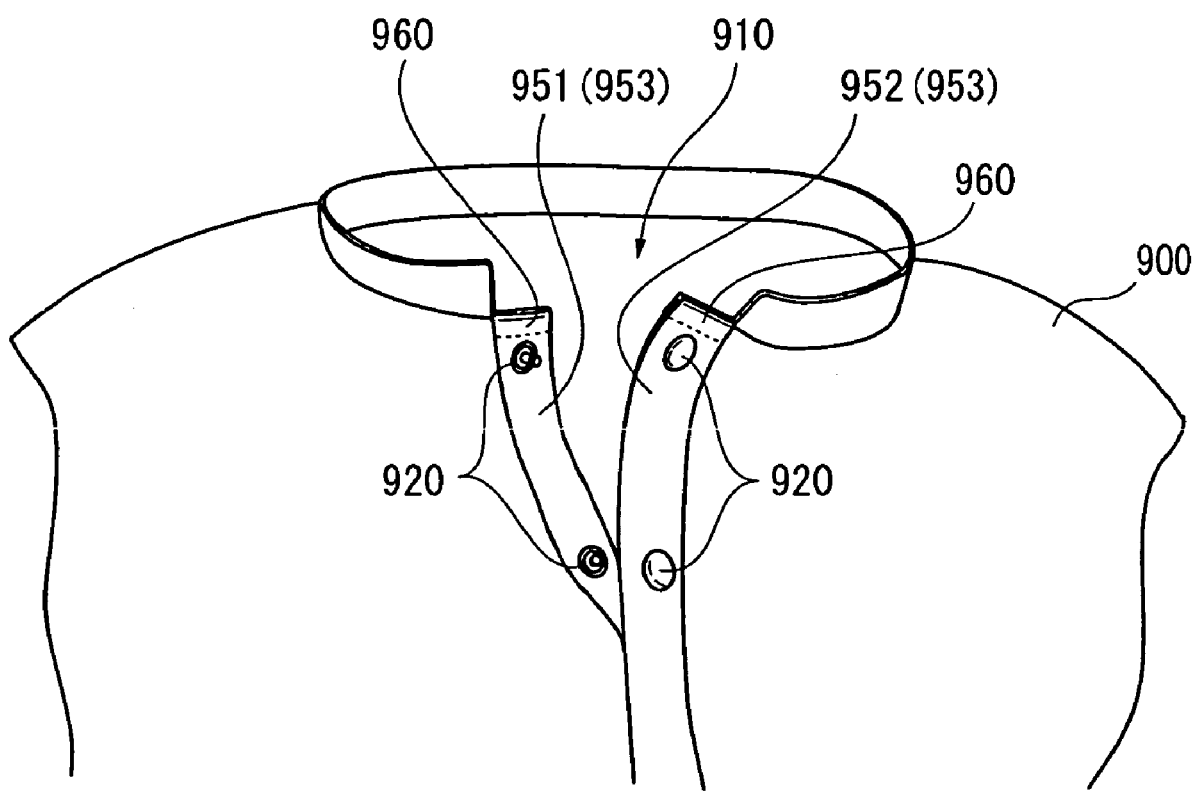
FIG. 10 is a view showing a snap fastener for fastening a fastening section of a garment for illustrating the conventional technology.
Figure 11:
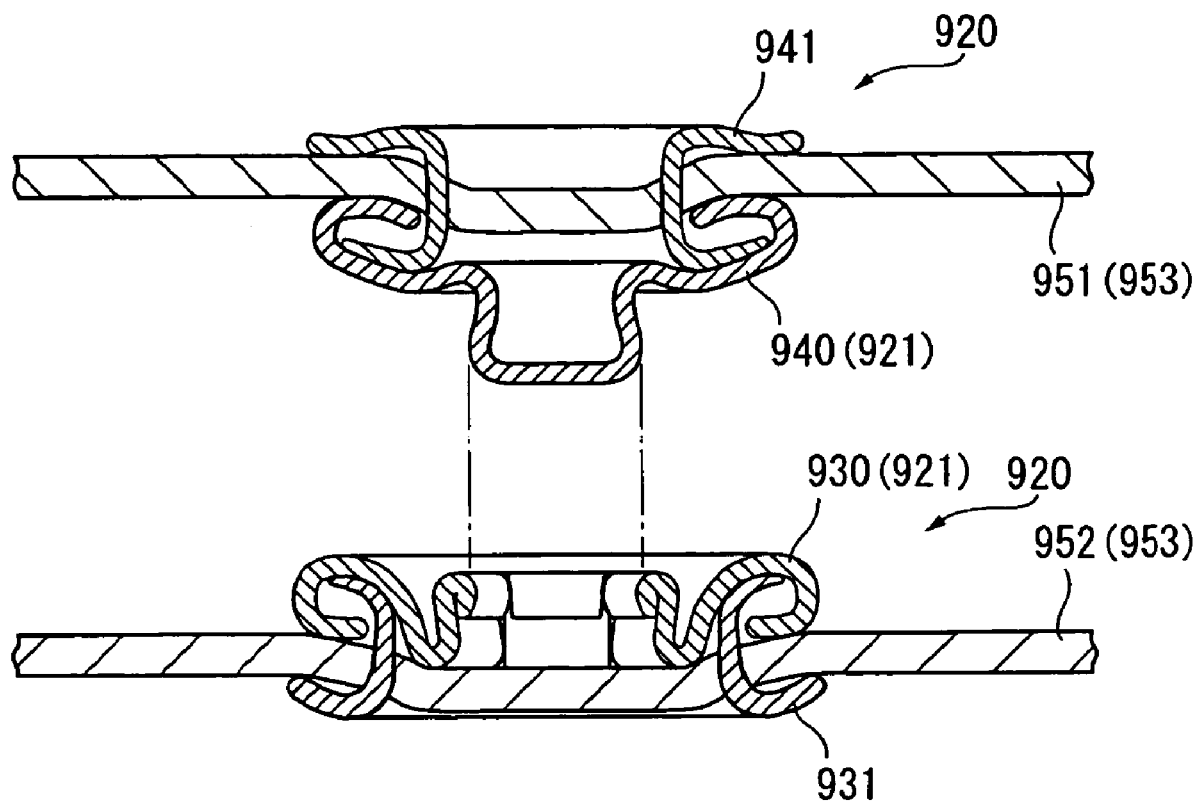
FIG. 11 is a view showing a snap member.
Figure 12:
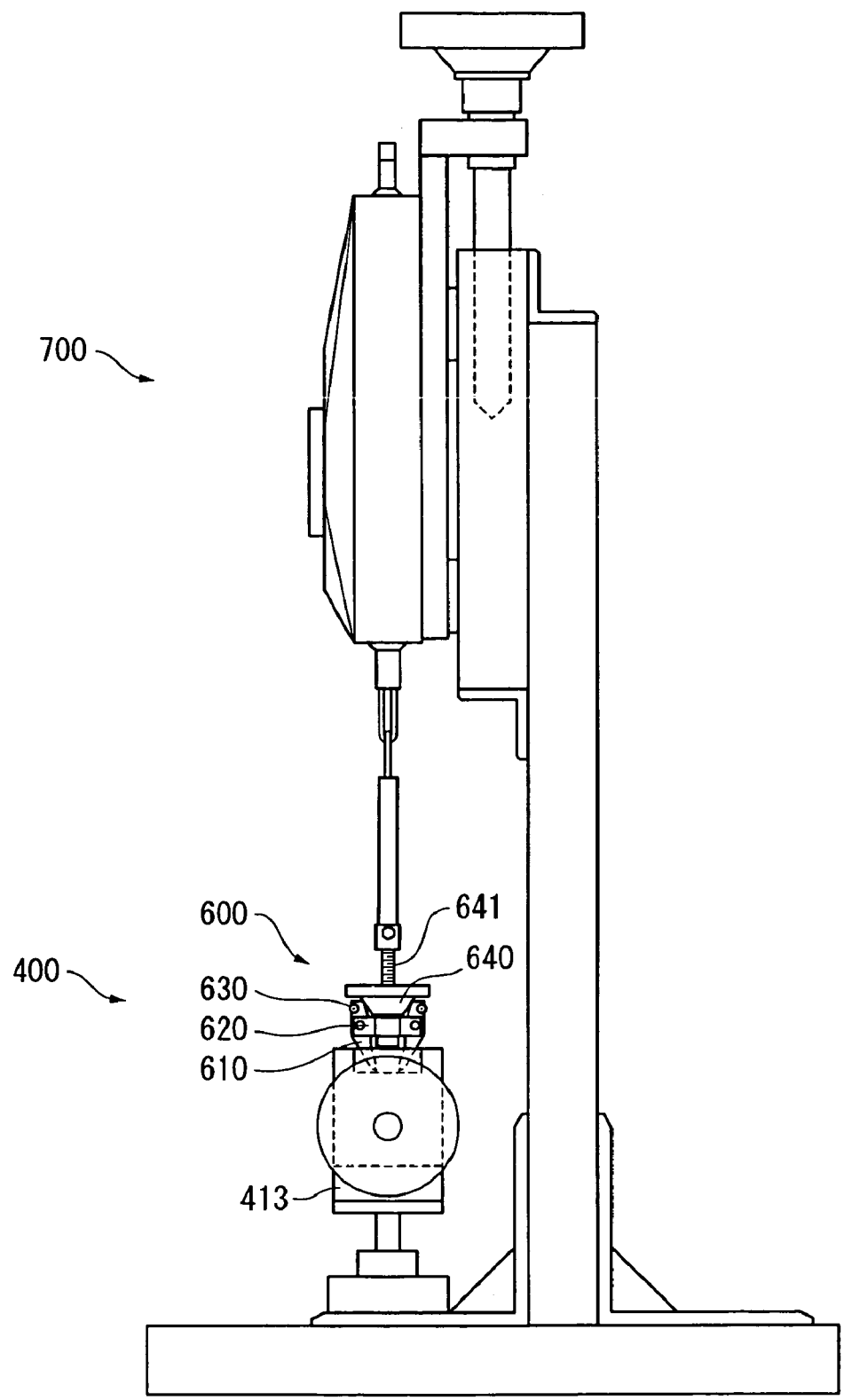
FIG. 12 is a side view showing a removing force measuring device based on the conventional technology.
Figure 13:
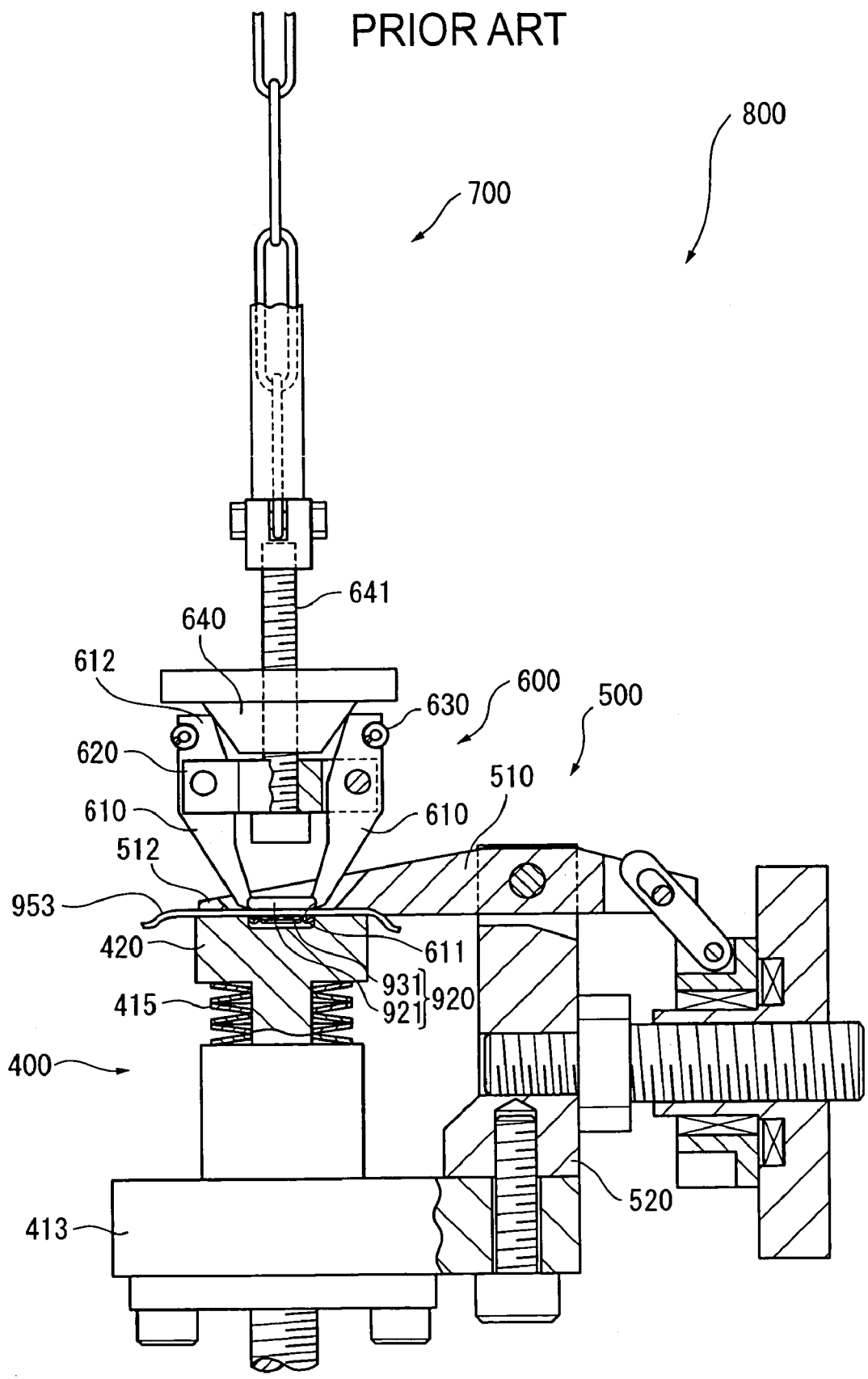
FIG. 13 is a partially enlarged view showing the removing force measuring device based on the conventional technology when viewed from the front side.
Figure 14:
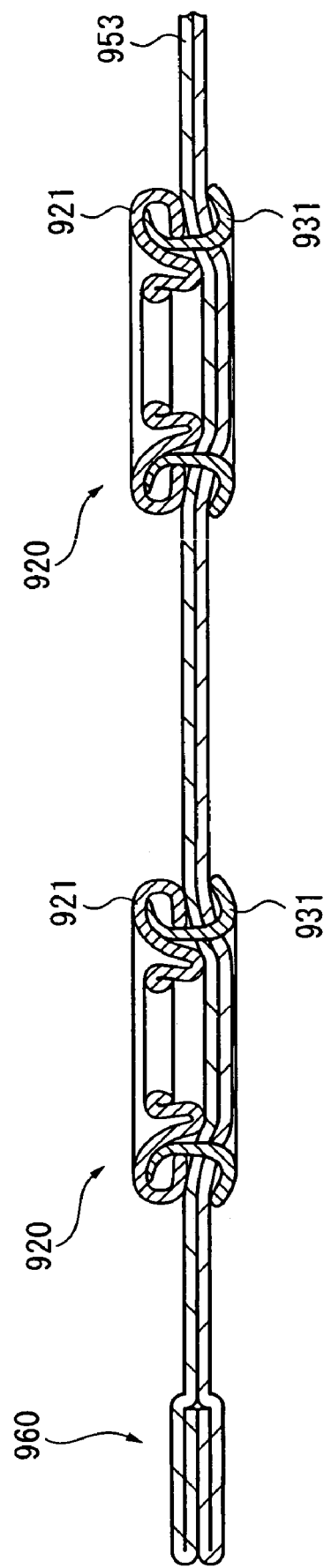
FIG. 14 is a view showing a fabric having a thick portion at an edge thereof.
Figure 15:
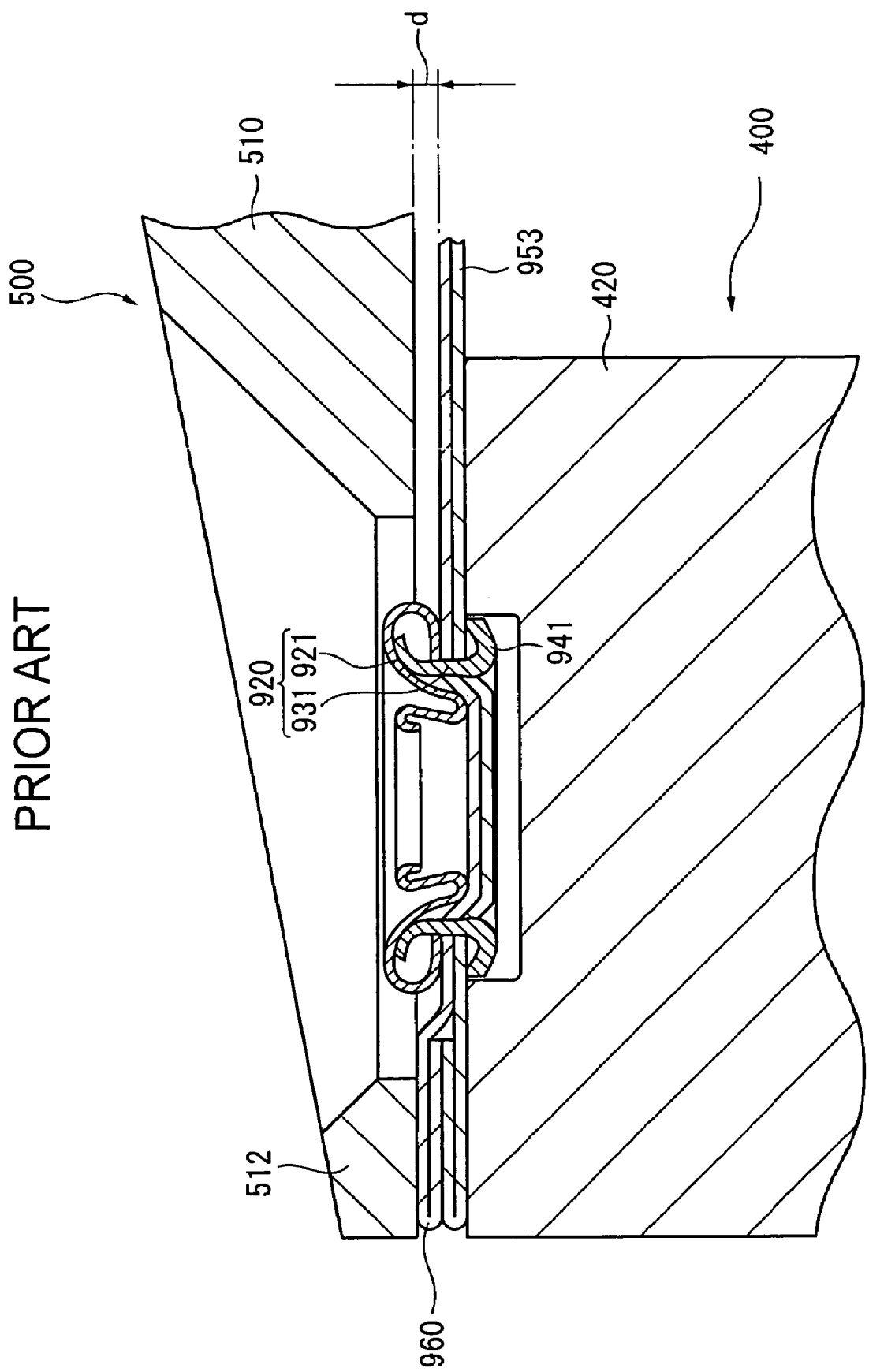
FIG. 15 is a view showing the state where a fabric having different thicknesses in different portions thereof is held by a holding unit based on the conventional technology.

In the embodiment described above, the fastening member is the snap member 921, but the fastening member is not limited to this configuration, and may be a button section 970, or any of a cap section 990, a rivet 980, or a prong member 931, 941 each for fastening the snap member 921 or the button section 970 to the fabric 953 as shown in FIG. 9A to FIG. 9C.

The spring section 415 may include a plurality of plate springs, or may include an elastic member made of such a material as rubber or urethane.

In the embodiment described above, the tensile force measuring unit pulls upward the restricting unit, but the tensile force measuring unit may pull the holding unit, and further the tensile force measuring unit may pull both of the restricting unit and holding unit in a direction in which the two components moves away from each other.

The priority application Number JP2004-135909 upon which this patent application is based is hereby incorporated by reference.

What is claimed is:

1. A removing force measuring device for measuring a removing force for a fastening member attached to a fabric; the device comprising:
a holding unit for holding the fabric around the fastening member;
a restricting unit for restricting the fastening member; and
a tensile force measuring unit for pulling at least either one of the restricting unit and the holding unit in a direction in which the restricting unit restricting the fastening member and the holding unit move away from each other while measuring a tensile force,
wherein the restricting unit comprises:
a die for mounting thereon the fabric with the fastening member attached thereto; and
a fabric presser unit for pressing the fabric mounted on the die to the die to hold the fabric together with the die, wherein the die comprises:
a frame holding section with a face facing against the fabric presser unit opened and having an accommodating section inside thereof;
a mounting base onto which the fastening member is mounted, the mounting base being provided in the accommodating section,
a viscoelastic section provided in the accommodating section around the mounting base, and
an elastic section laminated on the viscoelastic section in the accommodating section around the mounting base and provided on the side of the fabric presser unit, the elastic section formed with an elastic member made of one of rubber, thermosetting elastomer, and thermoplastic elastomer; and wherein the elastic member is harder than the viscoelastic section.

2. The removing force measuring device according to claim 1,
wherein an elastic holding member formed with an elastic member is provided on a face of the fabric presser unit contacting the fabric.

3. The removing force measuring device according to claim 1,
wherein a protruding section and a concave section engaging with each other are respectively provided on opposing faces of the fabric presser unit and the elastic member.

4. The removing force measuring device according to claim 1, wherein an upper side of the elastic section protrudes above a periphery of an opening of the frame holding section.

5. The removing force measuring device according to claim 1, wherein the viscoelastic section and the elastic section respectively have a central hole at the center thereof, the mounting base being inserted into the central hole.

6. A holding unit for holding a fabric comprising:
a die for mounting thereon the fabric with a fastening member attached thereto; and
a fabric presser unit for pressing the fabric mounted on the die to the die from a side opposite to the die and holding the fabric together with the die,
wherein the die comprises:
a frame holding section with a face facing the fabric presser unit opened and having an accommodating section inside thereof;
a mounting base onto which the fastening member is mounted, the mounting base being provided in the accommodating section,
a viscoelastic section provided in the accommodating section around the mounting base, and
an elastic section laminated on the viscoelastic section in the accommodating section around the mounting base and provided on a side of the fabric presser unit, and the elastic section formed with an elastic member made of one of rubber, thermosetting elastomer, and thermoplastic elastomer; and wherein the elastic member is harder than the viscoelastic section.

7. The holding unit according to claim 6,
wherein an elastic holding member formed with an elastic member is provided on a face of the fabric presser unit contacting the fabric.

8. The holding unit according to claim 6,
wherein a protruding section and a concave section engaging with each other are respectively provided on opposing faces of the fabric presser unit and the elastic member.

9. The holding unit according to claim 6, wherein an upper side of the elastic section protrudes above a periphery of an opening of the frame holding section.

10. The holding unit according to claim 6, wherein the viscoelastic section and the elastic section respectively have a central hole at the center thereof, the mounting base being inserted into the central hole.

* * * * *